(12) United States Patent
Mishra et al.

(10) Patent No.: US 8,109,187 B2
(45) Date of Patent: Feb. 7, 2012

(54) TISSUE HARVESTING DEVICE AND METHOD

(75) Inventors: Ajit Mishra, San Antonio, TX (US); Charles Seegert, San Antonio, TX (US); Makoto Ohira, Newton, MA (US)

(73) Assignee: KCI Licensing, Inc., San Antonio, TX (US)

( * ) Notice: Subject to any disclaimer, the term of this patent is extended or adjusted under 35 U.S.C. 154(b) by 1098 days.

(21) Appl. No.: 11/702,766

(22) Filed: Feb. 6, 2007

(65) Prior Publication Data

US 2007/0179516 A1    Aug. 2, 2007

Related U.S. Application Data

(63) Continuation of application No. 10/442,488, filed on May 21, 2003, now abandoned, and a continuation-in-part of application No. 10/379,342, filed on Mar. 3, 2003, now Pat. No. 7,651,507.

(51) Int. Cl.
   *B23D 25/12* (2006.01)

(52) U.S. Cl. ............... 83/343; 83/663; 83/862; 83/863; 83/37; 83/39; 83/52; 83/284; 83/321; 83/331; 83/469; 83/495

(58) Field of Classification Search ............ 83/663, 83/862, 863, 37, 39, 52, 284, 321, 331, 469, 83/495
See application file for complete search history.

(56) References Cited

U.S. PATENT DOCUMENTS

| | | | | |
|---|---|---|---|---|
| 3,076,461 | A | 2/1963 | Meek et al. | 128/305 |
| 3,076,462 | A | 2/1963 | Meek et al. | 128/305 |
| 3,613,242 | A | 10/1971 | Hill et al. | |
| 3,640,279 | A | 2/1972 | Brown et al. | 128/305 |
| 4,340,342 | A * | 7/1982 | Kim | 425/72.1 |
| 4,773,418 | A | 9/1988 | Hettich | 128/305.5 |
| 5,196,020 | A | 3/1993 | Atkinson et al. | 606/132 |
| 5,219,352 | A * | 6/1993 | Atkinson | 606/132 |
| 6,063,094 | A | 5/2000 | Rosenberg | 606/132 |
| 6,248,114 | B1 | 6/2001 | Ysebaert | |
| 7,156,007 | B1 * | 1/2007 | Albin et al. | 83/302 |
| 2001/0029380 | A1 * | 10/2001 | Ysebaert | 606/132 |
| 2004/0172045 | A1 | 9/2004 | Eriksson et al. | 600/36 |

FOREIGN PATENT DOCUMENTS

| | | |
|---|---|---|
| FR | 1 497 723 | 10/1967 |
| WO | WO 88/07426 | 10/1988 |
| WO | WO 2004/075764 | 9/2004 |

OTHER PUBLICATIONS

"The International System of Units (SI)," *Organisation Intergouvernementale de la Convention du Metre*, pp. 117 and 131, $8^{th}$ edition, 2006.
"The microtome: function and design," Copyright Woods and Ellis, 2000. http://home.primus.com.au/royellis/microt/microt.htm; Accessed Jul. 25, 2005.
International Search Report and Written Opinion issued in International Application No. PCT/US04/15887, mailed Oct. 7, 2008.
Kreis et al., "Expansion techniques for skin grafts: comparison between mesh and Meek island (sandwich-) grafts," *Burns*, 20:S39-S42, 1994.
Lin et al., "Microskin grafting of rabbit skin wounds with Biobrane overlay," *Burns*, 18:390-394, 1992.
Office Action issued in U.S. Appl. No. 10/379,342, mailed Feb. 17, 2005.
Office Action issued in U.S. Appl. No. 10/379,342, mailed Oct. 4, 2005.
Office Action issued in U.S. Appl. No. 10/442,488, mailed Aug. 18, 2006.
Office Action issued in U.S. Appl. No. 10/442,488, mailed Jan. 26, 2006.
Office Action issued in U.S. Appl. No. 10/442,488, mailed Jul. 27, 2005.
Office Action issued in U.S. Appl. No. 10/442,488, mailed Jun. 8, 2005.
Zermani et al., "Micrografting in the treatment of severely burned patients," *Burns*, 23:604-607, 1997.

* cited by examiner

*Primary Examiner* — A M Ford
*Assistant Examiner* — S E Fernandez
(74) *Attorney, Agent, or Firm* — Fulbright & Jaworski L.L.P.

(57) ABSTRACT

A tissue harvesting method and device for obtaining micrograft tissue particles within the size range of 50-1500 microns, and more preferably 500-1000 microns, and most preferably 600 microns. The particles may be processed after a piece of donor tissue has been excised from the donor site, or processed into the desired size directly at the donor site, and thereafter excised. Cutters having blades or cutting edges spaced in the range of 50-1500 microns are utilized to obtain particles within the desired size range. An elastomer is positioned between the cutting edges to push the excised particles out of the blades for ease of use.

3 Claims, 5 Drawing Sheets

TISSUE HARVESTING DEVICE AND METHOD

CROSS-REFERENCE TO RELATED APPLICATION

This is a division of co-pending application Ser. No. 10/442,488 entitled "Tissue Harvesting Device and Method," filed May 21, 2003, which is a continuation-in-part of co-pending application Ser. No. 10/379,342 entitled, "Tissue Processing System," filed Feb. 3, 2003; the prior applications are herewith incorporated by reference in their entirety.

FIELD OF THE INVENTION

The invention relates to a device and method for harvesting dermal tissue. More particularly, this invention relates to a device and method for extracting small particles of dermal tissue for transplantation to a recipient site.

BACKGROUND OF THE INVENTION

Traditional skin grafting is accomplished by taking a thin slice of dermal tissue from a donor site in order to cover a wound site, such as a burn area. In some instances, the slice of dermal tissue is meshed to expand its size, creating a meshed graft. Traditional devices used to harvest the tissue from the donor site include dermatomes for removing a thin slice of the upper layers of skin from a donor site. The slice is then meshed using traditional techniques to create and expand the sheet of skin tissue that gives the slice a weave-like appearance. The purpose of expanding the skin from the donor site is to increase the amount of area on a recipient site that can be covered by the donor site. Some of the most desirable expansion ratios currently available are 6:1. That is, under the most ideal conditions, skin taken from a donor site would be able to cover a recipient site that is six times larger than the donor site.

Traditional meshed grafting techniques have been shown to yield 90% viability at the donor site. A slightly lower viability rate occurs for non-meshed sheet grafts, mostly due to fluid accumulation under the sheet graft. Factors that lead to graft failure include poor circulation, unclean wounds, patient interference with the graft dressing, obesity, and smoking. Additionally, in at least approximately 10% of cases, infection at the donor site occurs. Although such donor site infections are not likely related to graft failure at the wound site, they still pose problems for both the patient and caregiver.

As mentioned, traditional meshing techniques yield a most favorable expansion ratio of 6:1. For example, a 1 cm$^2$ donor site can cover a 6 cm$^2$ wound site. While greater ratios of 9:1 and 12:1 may be possible using meshing techniques, there is also a significant delay in epithelialization with such ratios.

Micro grafting techniques, in which the donor tissue is actually minced in order to achieve a greater than 10:1 expansion ratio, are known in the art. Such techniques allow for a much greater coverage area from a small donor site. However, traditional techniques are cumbersome, and often the viability of the cells is compromised to such an extent that sometimes less than 50% of the cells are viable when applied to the wound site. Additionally, traditional techniques have thus far been inadequate in producing viable cells in the range of 500-1500 microns.

Traditional micrograft techniques, dating back to 1963, utilized minced skin that is between $\frac{1}{8}^{th}$ inch (approximately 3 mm, or 3000 microns) or $\frac{1}{16}^{th}$ inch (approximately 1.5 mm, or 1500 microns) in size. However, disadvantages of using pieces larger than 1500 microns have been noted. Among the disadvantages are that many of the cells are trapped within the pieces of skin, and are thus unable to proliferate or produce new cells required to form new skin. Furthermore, if such large pieces of skin are to be transplanted, the epidermis side of each piece has to be oriented upwards, and the dermis side oriented downwards. This makes the procedure tedious and impractical. Also, the appearance of the new skin that is produced using particles of this size is poor, often having a cobblestone appearance.

Other micrografting techniques have utilized minced skin that is 200 to 500 microns in size. While sometimes producing cosmetically better grafts over the larger micrografts, many of the cells contained in the particles are rendered non-viable by the process of producing cells of such a small size.

It is therefore an object of this invention to provide a system for obtaining and processing tissue samples from a donor site on the order of 50-1500 microns in size, such that the vast majority of tissue processed at this size is viable when transplanted to a recipient site. It is a further object of the present invention to strike the ideal balance between cell viability and cell proliferation between the size range of 500-1500 microns, and most preferably 600 microns, which has heretofore not been achieved.

Additional objects of the present invention include a significant reduction in the size of the donor site as compared to traditional mesh-graft procedures; minimizing scarring of the graft site as compared to traditional mesh-graft procedures; improvement of the pliability of tissue in the graft site; improvement of the cosmetic appearance of the graft site as compared to current methods; and improvement of graft "take."

SUMMARY OF THE INVENTION

In accordance with the foregoing objects, the present invention generally comprises a device for harvesting tissue from a donor site into particles in the size range of 50-1500 microns, and most preferably about 600 microns, such that the particles may produce an expansion ratio, or cell proliferation, of at least 6:1 and up to or over 20:1.

The present invention includes a method for cutting and removing tissue from a donor site. The typical donor site may be equivalent to a split—thickness—skin graft ("STSG"). A traditional dermatome may be utilized to obtain the donor sample, or STSG, which is then processed into smaller micrografts between 50-1500 microns in size. More preferably, the micrografts are processed into sizes between 500 microns and 1500 microns, and most preferably to about 600 microns, which has been shown to yield the greatest viability and proliferation. A cutter is utilized to process the tissue into the desired size. Alternatively, the donor tissue may be processed into the desired size directly on the donor site, and thereafter removed from the donor site.

The present invention also includes a cutter for processing the tissue into the desired size range. Several alternative cutters may be utilized in accordance with the present invention, including roller cutters. In one embodiment, a roller have having a square-shaped grid pattern of raised edges is used to achieve tissue particles of the desired size. Alternatively, dual rollers may be utilized, in which each roller has a series of evenly spaced parallel raised cutting edges, which are oriented perpendicular to the raised edges on the opposing roller. The donor tissue or STSG may be passed between the rollers, or the rollers may be pressed against a single surface of the donor tissue.

Other alternative cutters include die-cast rigid sheets, which may be flat or concave. The rigid sheet is pressed to the donor tissue manually or by means of a reciprocating roller. The cutting edges of the rigid sheet include a raised, square-shaped grid pattern, or alternatively, a series of opposing facing, raised concave cutting edges.

Cutters that may be utilized to process the donor tissue directly at the donor site include bundled capillary tubes, having a sharpened edge. Other cutters for processing donor tissue that has already been excised from the donor site include a cylindrical press cutter.

Removing the tissue from the cutters, after it has been processed into the desired size, is accomplished by positioning an elastomer, such as rubber or other flexible material, between the cutting surfaces of the cutters. As the cutter is pushed into the donor tissue, the elastomer retreats from the cutting edge to allow the tissue to be cut. As pressure is relieved from the cutter, the elastomer returns to its original position, thereby pushing the cut tissue out from the cutting edges.

The foregoing has outlined some of the more pertinent objects of the present invention. These objects should be construed to be merely illustrative of some of the more prominent features and applications of the invention. Many other beneficial results can be attained by applying the disclosed invention in a different manner or by modifying the invention as will be described. Accordingly, other objects and a fuller understanding of the invention may be had by referring to the following Detailed Description of the Invention, which includes the preferred embodiment

BRIEF DESCRIPTION OF THE DRAWINGS

These and other features and advantages of the invention will now be described with reference to the drawings of certain preferred embodiments, which are intended to illustrate and not to limit the invention, and wherein like reference numbers refer to like components, and in which.

DESCRIPTION OF THE INVENTION

Figure 1:
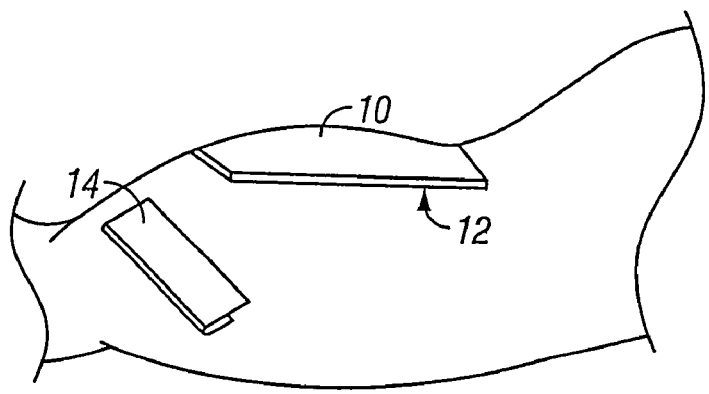
FIG. 1 is a perspective view of a donor tissue excised from a donor site using traditional methods.

Although those of ordinary skill in the art will readily recognize many alternative embodiments, especially in light of the illustrations provided herein, this detailed description is exemplary of the preferred embodiment of the present invention as well as alternate embodiments, the scope of which is limited only by the claims that may be drawn hereto.

Referring now to the drawings, the details of preferred embodiments of the present invention are graphically and schematically illustrated. Like elements in the drawings are represented by like numbers, and any similar elements are represented by like numbers with a different lower case letter suffix.

Figure 2:
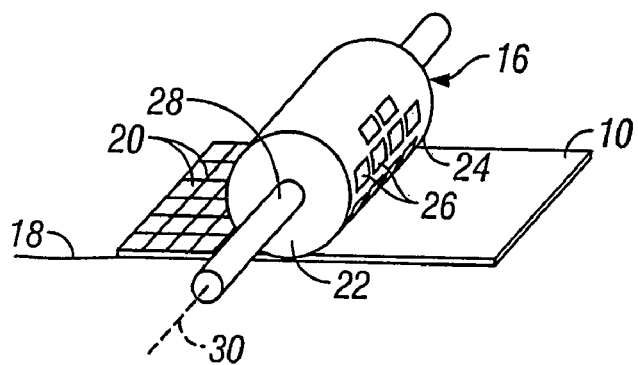
FIG. 2 is a perspective view of a cylindrical roller cutter of the present invention.
Figure 3:
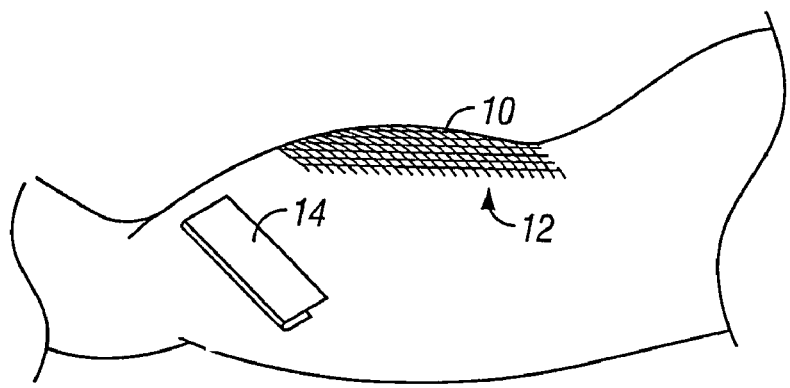
FIG. 3 is a perspective view of donor tissue processed into the desired size directly at the donor site in accordance with the present invention.

As illustrated in FIG. 1, a donor tissue sample 10, such as a split-thickness-skin graft ("STSG") may be removed from a healthy region of skin tissue 12 using traditional techniques, such as by running a dermatome 14 across the surface of the donor site 12. The donor tissue 10 is positioned on a flat surface 18, so that the cutter 16 of the present invention may be applied to it, as is shown in FIG. 2, in order to process the tissue into the desired size. In the preferred embodiment, the donor tissue 10 is processed into the desired size range of between 50-1500 microns$^2$, more preferably between 500-1000 microns$^2$, and most preferably 600 microns$^2$. Alternatively, the donor tissue 10 may be processed into the desired size or size range directly at the wound site 12, as depicted in FIG. 3. A dermatome 14, or similar traditional device, may be used to excise the processed tissue particles 10 from the donor site 12.

After the donor tissue is removed from the donor site, the tissue is processed by the tissue processor 16, as illustrated in FIGS. 2A and 2B. In an alternative embodiment, the tissue processor 16 cuts the donor tissue at the donor site 10 directly. The tissue processor is comprised of a series of sharpened blades 18 arranged in parallel to one another and fixed along an axis 20. The distance 22 between the blades 18 may be adjusted according to the desired size of the tissue sample to be obtained. The preferred distance 22 between each blade 18 is in the range of about 250 microns to 1000 microns. The most preferable distance 22 is one of about 16 of the present invention for processing donor tissue 10 into particles 20 of the desired size. The cutter 16 consists of a cylindrical roller 22 in which the cutting surface 24 consists of a square-shaped grid pattern of raised edges 26, that form blades for cutting the donor tissue 10 into particles 20 of the desired size. The roller 22 is pressed onto the donor tissue 10 manually, such as by handles 30 attached along the longitudinal axis 28 of the roller 22, or by an electromechanical actuator (not shown), such as an electric motor and axle along the longitudinal axis 28, similar to that used in traditional dermatomes known in the art.

Figure 4A:
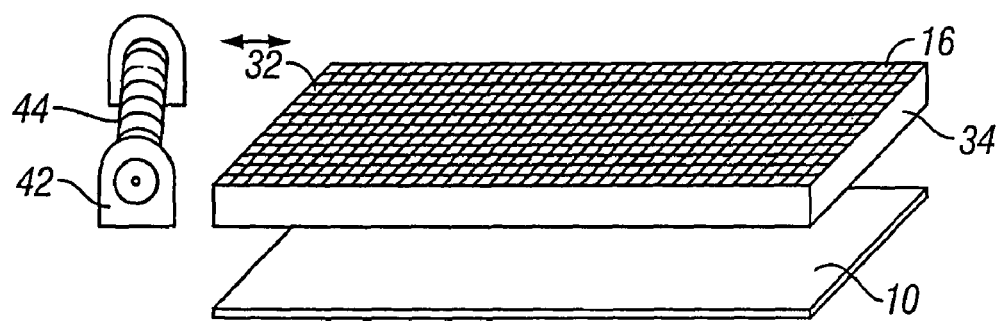
FIGS. 4A, 4B, and 4C are perspective views of a rigid sheet cutter of the present invention.
Figure 4B:
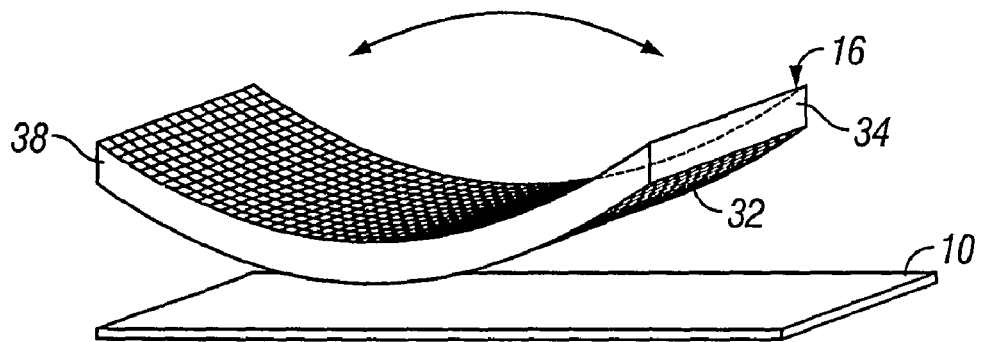
Figure 4C:
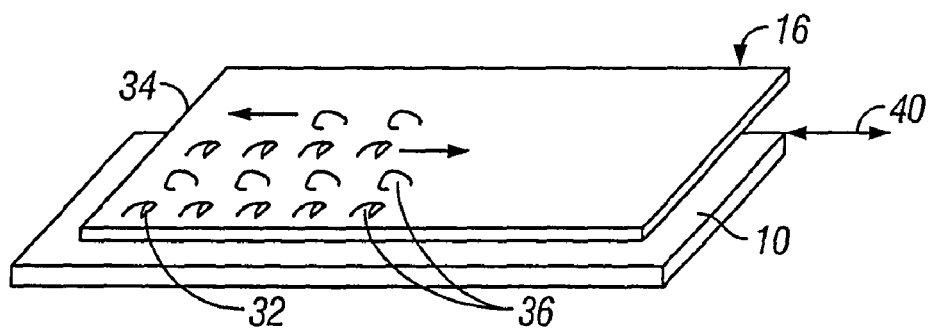

An alternative embodiment of the cutter 16, as illustrated in FIGS. 4A, 4B, and 4C, includes a rigid sheet 34 having a plurality of raised cutting edges 32. The rigid sheet 34 may be a die as shown in FIGS. 4A and 4B, in which the cutting edges 32 form a square-shaped grid pattern, in which each grid is the size of the desired particle to be cut from the donor tissue 10. Alternatively, the cutting edges 32 may consist of a series of oppositely facing, raised concave cutters 36, as shown in FIG. 4C. The rigid sheet 34 may be flat, as shown in FIG. 4A, or concave to aid in manual pressing of the cutter 16 to the donor tissue 10, as shown in FIG. 4B. In such an embodiment, the cutting edges are positioned on the outer curve 38 of the rigid sheet 34.

The particles may be extracted from the donor tissue after application of the rigid sheet 34 cutter 16 by oscillating the sheet 34, such as by a piezo-electric driver, along a vertical axis 40, as illustrated in FIG. 4C. Alternatively, the rigid sheet 34 may be pressed onto the donor tissue 10 manually. Other alternative pressing means include use of an arbor (not shown), such as an axle press known in the art, or by means of a roller actuator 42, that presses the sheet 34 against the donor tissue 10 as the roller 44 of the actuator 42 is passed across the surface of the rigid sheet 34, as shown in FIG. 4A.

Figure 5:
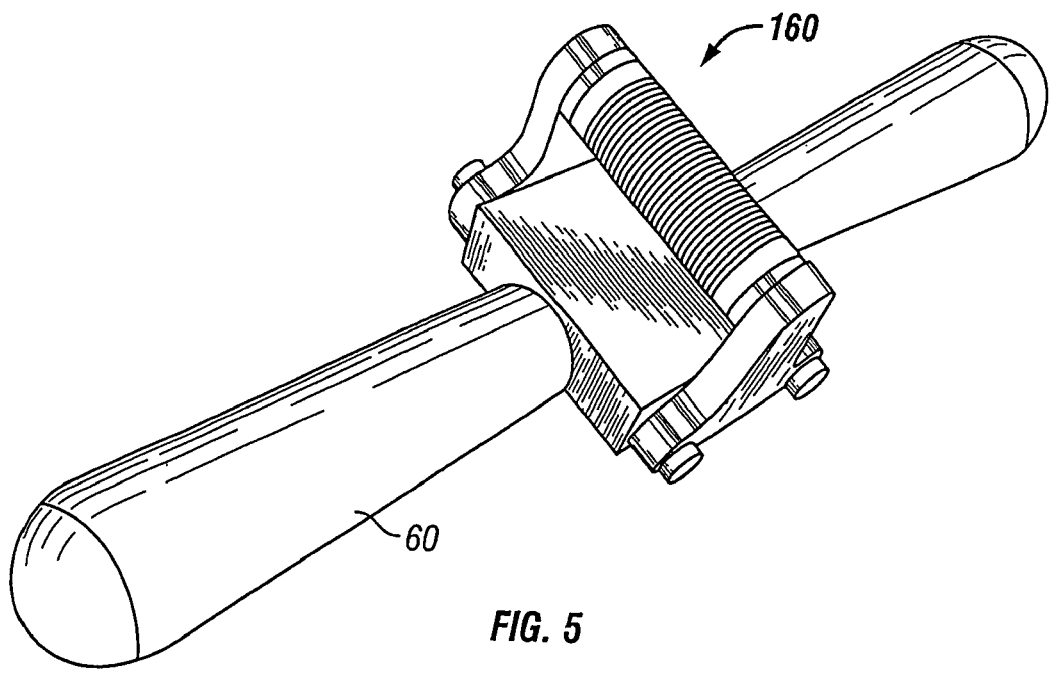
FIG. 5 is a perspective view of a circular blade cutter of the present invention.

Turning now to FIG. 5, there is illustrated a further embodiment of the cutter 16. The cutter is comprised of a series of sharpened circular blades 50 arranged in parallel to one another and fixed along an axis 52. A handle 60 may be positioned along an opposing axis 62. The distance 54 between the blades 50 may be adjusted according to the desired size of the tissue sample to be obtained. The preferred distance 54 between each blade 50 is in the range of about 50 microns to 1500 microns. The more preferable distance 54 is between about 500 microns and 1000 microns, and most preferably 600 microns. In the preferred embodiment, the space 54 between blades 50 may be adjusted to within the preferred distances mentioned, or alternatively, fixed to a distance within the preferred distances mentioned. The distance 54 between the blades 50 allows for uniform tissue particles to be produced at the ideal range of 50 square microns to 1500 square microns. As mentioned, tissue particles within the desired range have been shown to yield the highest expansion ratio while retaining the greatest viability.

Figure 6A:
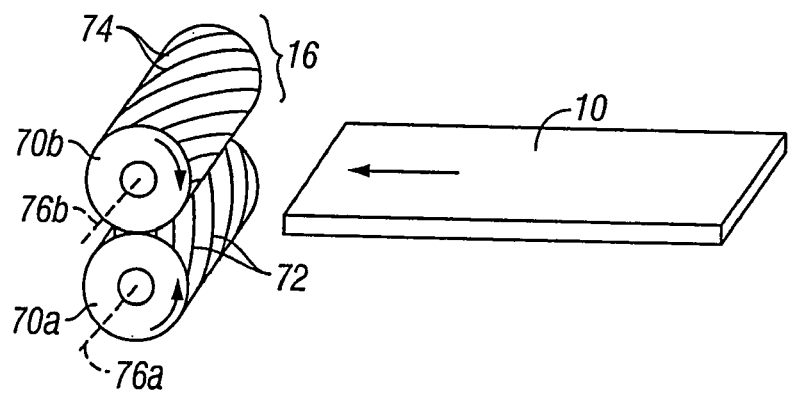
FIGS. 6A and 6B are perspective views of dual roller cutters of the present invention.
Figure 6B:
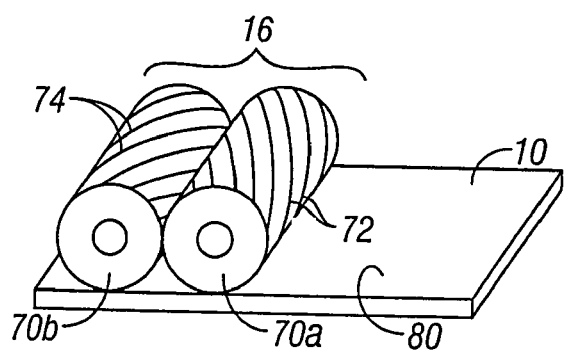

FIGS. 6A and 6B illustrate a further embodiment of the cutter 16, which consists of a pair of cylindrical rollers 70a, 70b. The first cylindrical roller 70a has a first set of raised, parallel cutting edges 72. The second cylindrical roller 70b has a second set of raised, parallel cutting edges 74 that are oriented approximately perpendicular to the first set of raised cutting edges 72. The cutting edges 72, 74 are separated by between about 50-1500 microns, and most preferably 600 microns. In the embodiment depicted in FIG. 6A, the donor tissue 10 is passed between the first and second rollers 70a, 70b, which are rotating in opposite directions around their respective axes of rotation 76a, 76b. Alternatively, and as depicted in FIG. 6B, the rollers 70a, 70b rotate in the same direction as they are pressed along the surface 80 of the donor tissue 10.

Figure 7:
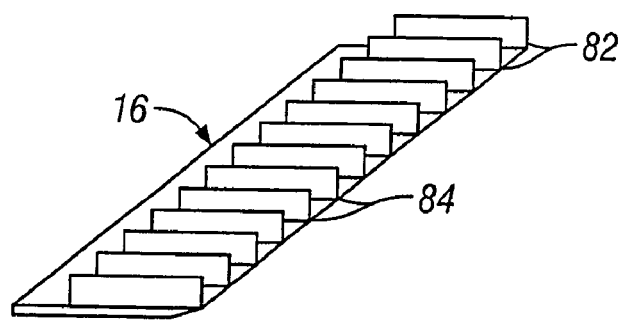
FIG. 7 is a perspective view of a stacked microtome cutter of the present invention.

Still another embodiment, as illustrated in FIG. 7, of the cutter 16 of the present invention consists of multiple microtomes 82 stacked and separated by a space 84 within the range of about 50-1500 microns, and most preferably 600 microns. The microtomes 82 are pressed against the donor tissue to achieve particles of the size desired.

Figure 8:
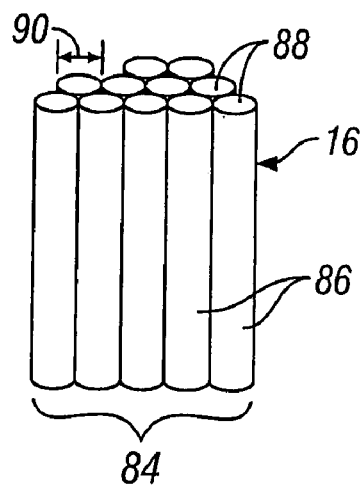
FIG. 8 is a perspective view of a bundled capillary tubes cutter of the present invention.

A further embodiment, shown in FIG. 8, of the cutter 16 of the present invention, consists of a bundle 84 of capillary tubes 86 having sharpened edges 88. The edges 88 are pressed into the donor tissue to extract particles of a size equivalent to the inner diameter 90 of the capillary tube 86, which is in the range of about 50-1500 microns, and most preferably 600 microns. An elastomer (not shown), such as soft rubber, may be positioned within each capillary tube 86 to aid in extraction of the particles after they have been cut from the donor tissue 10. As the capillary tube 86 is pushed into the tissue, the elastomer retreats from the edges 88 of the tube 86, allowing the tissue to be cut. As pressure is relieved, the elastomer returns to its original position within the tube, pushing the cut tissue particles out of the tubes 86.

Figure 9:
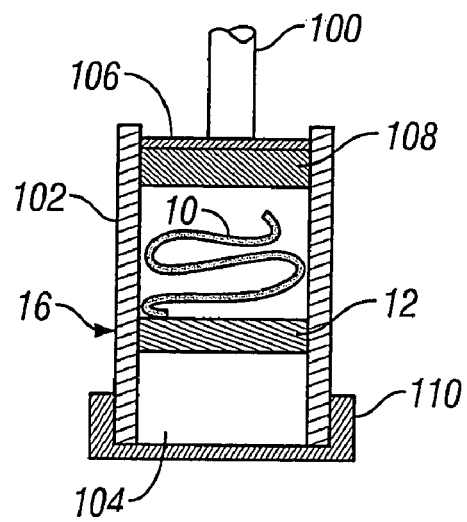
FIG. 9 is a cross-sectional view of a cylindrical press cutter of the present invention.

A cylindrical press 100, as shown in FIG. 9, may be utilized to cut tissue into a desired size within the range of 50-1500 microns, or preferably 600 microns, after the donor tissue 10 has been removed from the donor site 12. The press 100 is housed within a housing 102 having an open proximal end 104 and a closed distal end 106, which is closed by the press 100 itself. An elastomer 108, such as rubber, is fixed to the press within the housing, and a removable cap 110 is positioned along the open proximal end 104 for catching the tissue particles after they have been cut. Multiple blades 112 are fixed within the housing 102 between the elastomer 108 of the press 100, and the open proximal end 104. The donor tissue 10 is placed within the housing 102 between the press 100, which is removable, and the blades 104. As the press 100 passes through the housing 102, the elastomer 108 contacts the tissue 10 and forces it into and through the blades 112. The particles, having been cut to the desired size, are trapped within the cap 104.

Figure 10:
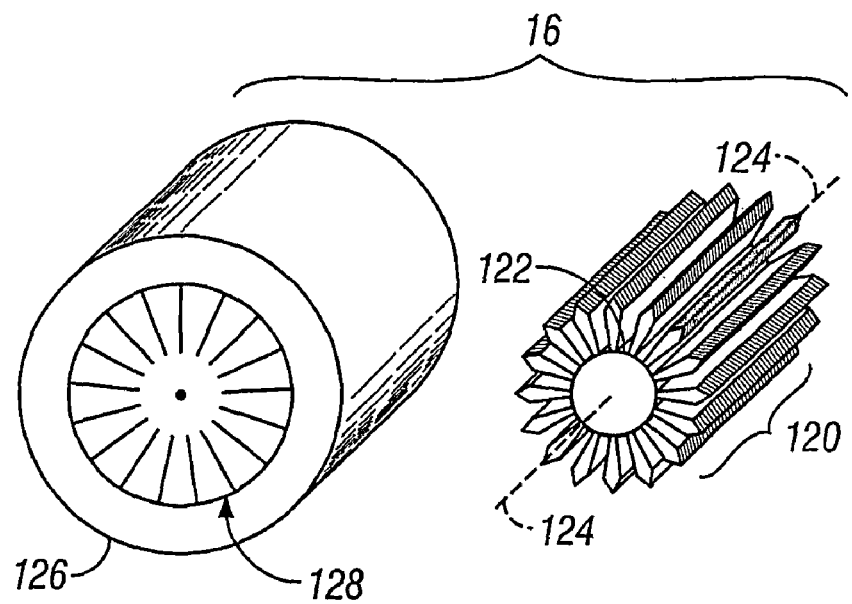
FIG. 10 is a perspective view of a stacked disc cutter of the present invention.

Still a further embodiment of the cutter 16 is illustrated in FIG. 10. The cutter may consist of multiple serrated discs 120. Slots 122 are formed within the discs 120, which are positioned along an axis 124. The discs 120 are fixed along the axis 124 such that a space of between 50-1500 microns, or preferably 600 microns, exists between each disc 120. A ring 126 of longitudinal blades 128 envelops the discs 120, and configured to pass between the serrations of the discs 120. Previously excised donor tissue 10 is placed between the discs 120, cutting them into the desired particle size as the ring 126 is passed over the discs 120.

Figure 11:
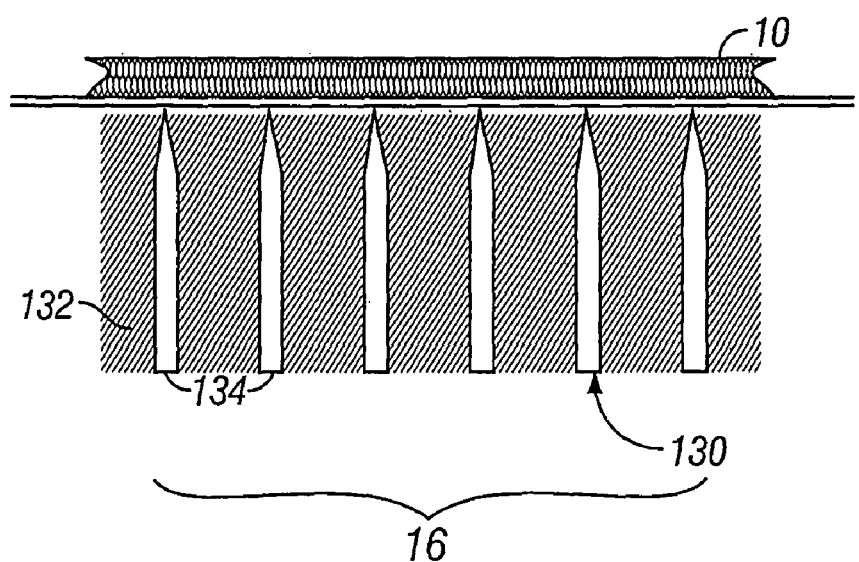
FIG. 11 is cross-sectional view of a tissue extraction means of the present invention.

Extraction of the particles from the blades or edges 130 of the cutter 16 is illustrated in FIG. 11. An elastomer 132 is positioned within the space 134 between the blades or edges 130. As pressure is exerted by the cutter 16 against the donor tissue 10, the elastomer 132 retracts. The cut tissue trapped in the space 134 between the blades 130 is forced out from the space 134 as pressure is relieved from the cutter 16 and the elastomer 132 returns to its original position.

The present invention includes a method of processing harvested donor tissue into micrograft particles within the size range of 50-1500 microns, and most preferably 600 microns. A further embodiment includes processing donor tissue to micrograft particles between 50-1500 microns, and most preferably 600 microns, directly at the donor site, and thereafter excising the particles from their contact points at the donor site using traditional means, such as a dermatome.

While the above description contains many specifics, these should not be construed as limitations on the scope of the invention, but rather as exemplifications of one or another preferred embodiment thereof. Many other variations are possible, which would be obvious to one skilled in the art. Accordingly, the scope of the invention should be determined by the scope of the appended claims and their equivalents, and not just by the embodiments.

Other features which are considered as characteristic for the invention are set forth in the appended claims.

Although the invention is illustrated and described herein as embodied in a Tissue Harvesting Device and Method, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

What is claimed is:

1. A cutter for processing tissue into particles suitable for transplantation, comprising:
   (i) a first cylindrical roller, having a first set of raised, parallel cutting edges; and
   (ii) a second roller having a second set of raised, parallel cutting edges; and
   (iii) wherein the first cylindrical roller is disposed proximal to the second roller such that a donor tissue can be passed between the first cylindrical roller and the second roller and wherein said first set of raised cutting edges is approximately perpendicular to said second set of raised cutting edges.

2. The cutter of claim 1 wherein said cutting edges of said first set of raised, parallel cutting edges are separated by between about 50 microns and 1500 microns.

3. The cutter of claim 1 wherein said cutting edges of said first set of raised, parallel cutting edges are separated by about 600 microns.

* * * * *